(12) United States Patent
Bubb

(10) Patent No.: US 7,326,217 B2
(45) Date of Patent: Feb. 5, 2008

(54) ORTHOPEDIC AND DENTAL IMPLANT SYSTEM AND METHOD

(76) Inventor: Stephen K. Bubb, 1257 Huntington Pl., Kansas City, MO (US) 64113

( * ) Notice: Subject to any disclaimer, the term of this patent is extended or adjusted under 35 U.S.C. 154(b) by 650 days.

(21) Appl. No.: 10/724,459

(22) Filed: Nov. 28, 2003

(65) Prior Publication Data

US 2005/0119666 A1 Jun. 2, 2005

(51) Int. Cl.
*A61B 17/58* (2006.01)
(52) U.S. Cl. ....................................................... 606/99
(58) Field of Classification Search ................... 606/99
See application file for complete search history.

(56) References Cited

U.S. PATENT DOCUMENTS

| | | | |
|---|---|---|---|
| 4,248,232 A | | 2/1981 | Engelbrecht et al. |
| 5,007,936 A | | 4/1991 | Woolson |
| 5,019,083 A | | 5/1991 | Klapper et al. |
| 5,045,054 A | | 9/1991 | Hood et al. |
| 5,112,338 A | | 5/1992 | Anspach, III |
| 5,151,099 A | * | 9/1992 | Young et al. ................. 606/27 |
| 5,169,399 A | | 12/1992 | Ryland et al. |
| D337,639 S | | 7/1993 | Beckman |
| 5,318,570 A | | 6/1994 | Hood et al. |
| 5,324,297 A | * | 6/1994 | Hood et al. .................... 606/99 |
| 5,352,230 A | * | 10/1994 | Hood ............................ 606/99 |
| 5,358,505 A | * | 10/1994 | Wuchinich .................... 606/99 |
| 5,456,686 A | * | 10/1995 | Klapper et al. ............... 606/99 |
| 5,507,833 A | | 4/1996 | Bohn |
| D372,309 S | | 7/1996 | Heldreth |
| 5,626,584 A | * | 5/1997 | Young .......................... 606/99 |
| 5,630,819 A | | 5/1997 | Ashby et al. |
| 5,800,546 A | | 9/1998 | Marik et al. |
| 5,846,244 A | | 12/1998 | Cripe |
| 6,113,618 A | | 9/2000 | Nic |
| 6,126,659 A | | 10/2000 | Wack |
| 6,190,392 B1 | | 2/2001 | Vandewalle et al. |
| RE37,358 E | | 9/2001 | Del Rio et al. |
| 6,500,209 B1 | | 12/2002 | Kolb |
| 6,503,281 B1 | | 1/2003 | Mallory |

(Continued)

OTHER PUBLICATIONS

Author Unknown, The Woodpecker, promotional literature for product manufactured by IMT (Integral Medizintechnik) and distributed by Minnestota Bramstedt Surgical, Inc., 1996.

*Primary Examiner*—Eduardo C. Robert
*Assistant Examiner*—Michael J Araj
(74) *Attorney, Agent, or Firm*—Mark E. Brown

(57) ABSTRACT

A system for removing osteal cement and prosthetic joint components in connection with a prosthetic joint revision includes a controller connected to and controlling operation of a transducer, such as a surgical saw or drill. A tool mounted on the transducer is adapted for engaging the prosthetic joint cement mantel and melting an engagement portion of same. The cement in the engagement portion is resolidified with the tool tip embedded therein. The tool thus bonds to the cement mantel, and is used for vibrating, softening and breaking up same when operation of the transducer resumes. An osteal cement and prosthetic device removal method includes the steps of melting an engagement portion of the osteal cement mantel, bonding a transducer-mounted tool to the cement mantel by resolidifying the cement engagement portion and reactivating the transducer for vibrating, softening and breaking up the cement mantel whereby it can be removed from the patient.

4 Claims, 19 Drawing Sheets

U.S. PATENT DOCUMENTS

2002/0099447 A1    7/2002   Mears et al.
2002/0116067 A1    8/2002   Mears et al.
2002/0183656 A1   12/2002   Levanoni et al.
2003/0097135 A1    5/2003   Penenberg

* cited by examiner

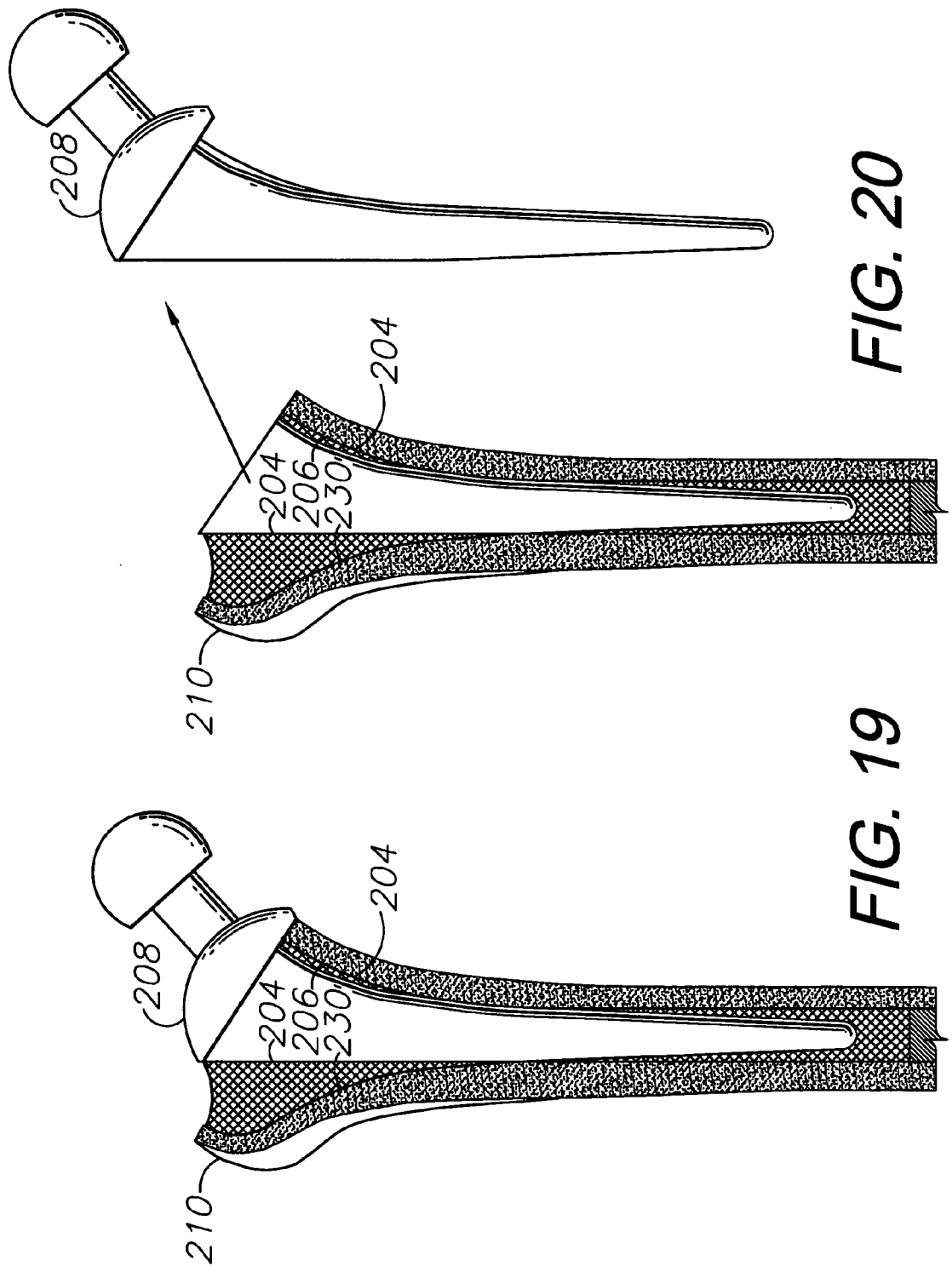

ORTHOPEDIC AND DENTAL IMPLANT SYSTEM AND METHOD

BACKGROUND OF THE INVENTION

1. Field of the Invention

The present invention relates generally to implant systems and methods for orthopedic and dental applications. More specifically, the present invention relates to implant insertion and extraction with couplings for attachment to manual and power force transducers with control over force variables.

2. Description of the Related Art

Many orthopedic procedures involve implants for replacing damaged and dysfunctional joints. For example, total joint replacement (TJR) and hemi arthroplasty (replacing one-half of the joint) procedures have been developed. Hips, knees, elbows, shoulders and wrists are commonly reconstructed with implants, such as prosthetic joints that are designed for optimal wear, comfort, biocompatibility and performance. Such replacement joint implants have benefited many patients by restoring their mobility and other functions.

Reconstructive dental procedures include installing implants such as prosthetic teeth, bridges, mandibles, temporomandibular (TMJ) joints and other dental prostheses. Significant improvements in dental function can be achieved for many patients using such procedures.

An important objective in designing orthopedic and dental implants and in performing implant procedures relates to effectively and permanently bonding the prosthetic components to patients' existing, viable bone and dental structure. For example, TJR orthopedic surgery typically involves removing damaged and degenerated existing joints and adjacent bone structure for replacement with prostheses. The remaining bone structure is preferably sound, dense and capable of withstanding dynamic loads in order to maximize patient function and mobility. A general objective of orthopedic and orthodontic surgery is to retain as much original, healthy bone structure as possible.

Orthopedic and orthodontic revision procedures are necessitated by prosthetic failures from various causes. For example, further deterioration and trauma can lead to prosthetic joint failures. Another problem relates to loosening and disengagement of the components. For example, orthopedic cement, which is commonly used to bond prosthetic components to bone, can loosen and disengage. Looseness and "play" in implants, such as prosthetic joints, can cause significant problems. These include patient discomfort and immobility. Moreover, such looseness can increase under dynamic loading, and can ultimately lead to complications associated with implant failure.

When revision procedures are indicated by such conditions, extracting existing implants and the cement mantels bonding same can present significant difficulties. Extracting prostheses that have been permanently bonded in place with high-strength adhesives can require substantial force, with resulting trauma and collateral damage. For example, perforated and cracked existing bone structures can result from forces associated with extracting failed prostheses.

Moreover, implants can become stuck during installation. For example, if the cavity formed for the implant shaft is too small, a test fit can result in immobility with resistance to both insertion and extraction. Extracting a stuck implant can require breaking the surrounding bone structure, with resulting complications.

The prior art has attempted to address some of the problems associated with orthopedic implant extractions. For example, the Engelbrecht et al. U.S. Pat. No. 4,248,232 discloses the use of a vibrating tool to soften the cement between nested components bonded together. The Hood et al. U.S. Pat. No. 5,045,054 discloses an ultrasound power generator adapted for coupling to endoprostheses and vibrating same to soften their adhesive bonds. Hood et al. disclose an ultrasonic tool for attachment to and removal of surgical components in U.S. Pat. No. 5,318,570. Vandewalle et al. U.S. Pat. No. 6,190,392 disclose an auger tool connected to an ultrasonic transducer/handpiece for extracting an osteal cement mantel.

Heretofore there has not been available an orthopedic and dental implant system and method with the advantages and features of the present invention.

SUMMARY OF THE INVENTION

In the practice of the present invention, systems and methods are provided for installing and extracting orthopedic and dental implants. In one aspect of the invention, a manual or power force transducer is coupled to an implant for imparting installation or extraction forces, ranging from low-amplitude vibrations to impact blows through a range of frequencies. The forces can act in either direction, i.e. insertion or extraction, or both in an alternating operational mode. The amplitudes of the forces can be varied, including amplitude differentials on insertion/extraction strokes. The forces can be linear reciprocating, rotorary reciprocating, oscillatory (side-to-side) or orbital.

In another aspect of the invention, a power source connects to a working tip adapted for melting an engagement portion of a cement mantel. Discontinuing the application of power to the working tip causes the cement to resolidify on and capture same. A second power application vibrates the entire homogenous portion of the cement loose for extraction.

In another aspect of the invention, the controller scans predetermined frequency, amplitude and other variable ranges and selects optimum values for such operating parameters based on feedback received from sensors connected to vibrating tools or patients. The sensors can detect current loading as a function of variable patient and system conditions.

BRIEF DESCRIPTION OF THE DRAWINGS

The drawings constitute a part of this specification and include exemplary embodiments of the present invention and illustrate various objects and features thereof.

FIGS. 19-22 are vertical, cross-sectional views of a femur, showing the removal of a femoral implant and the cement mantel associated therewith according to an aspect of the method of the present invention.

DETAILED DESCRIPTION OF THE PREFERRED EMBODIMENT

Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
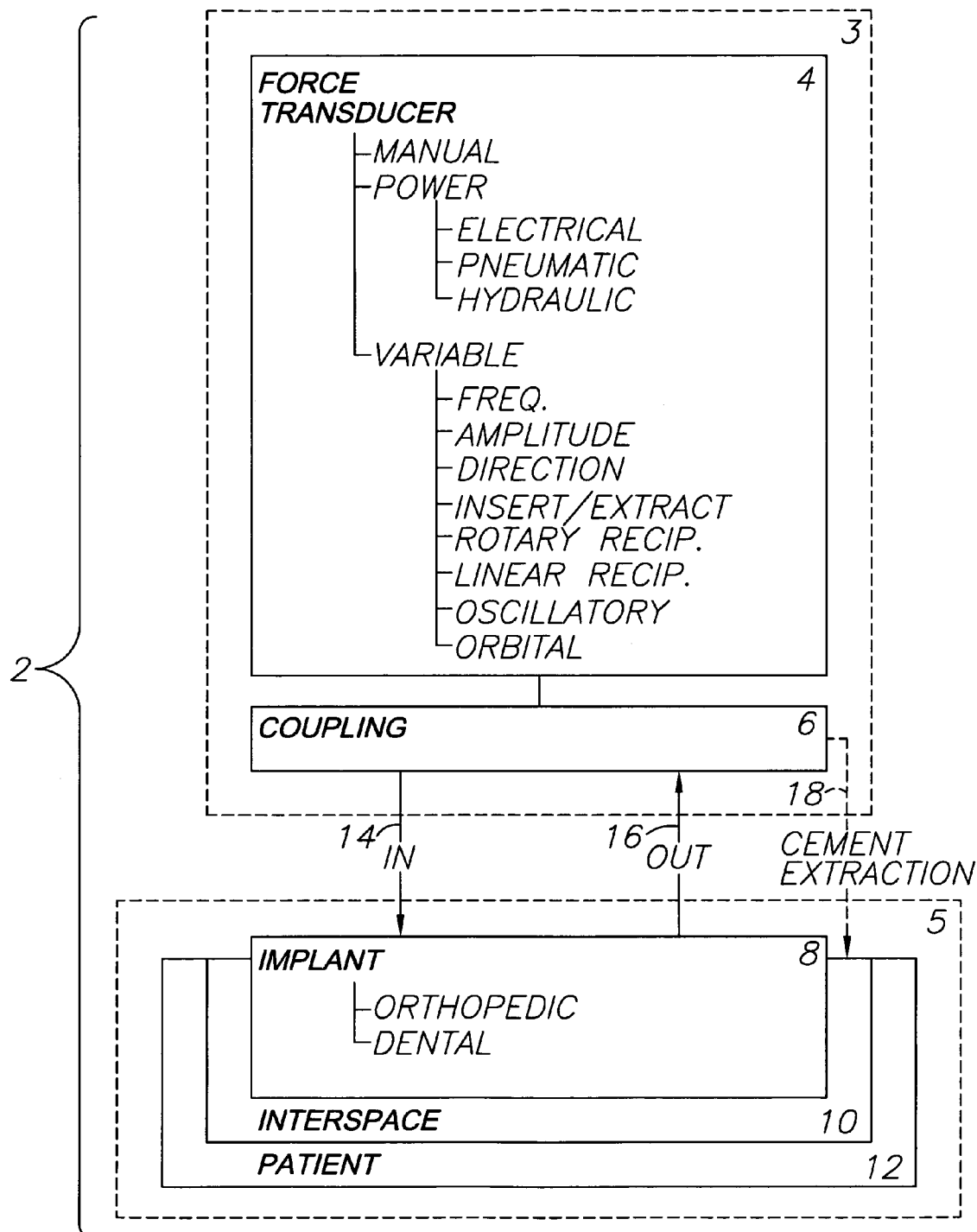
FIG. 1 is a schematic, block diagram of an implant system embodying the present invention.

Referring to FIG. 1, the reference numeral 2 generally designates an orthopedic and dental implant system embodying an aspect of the present invention. The system 2 generally includes an external subsystem 3 including a force transducer 4, which can comprise a manual device, such as a slaphammer, or an electrical, pneumatic or hydraulic power device. The transducer 4 is adapted for variable operation, including such variable operating parameters as frequency, amplitude, direction (i.e. in or out with respect to the patient) and insertion and/or extraction. The transducer 4 can apply linear reciprocating, rotary reciprocating, oscillatory (side-to-side) or orbital force. A coupling 6 is connected to the force transducer 4. The coupling 6 and its ancillary components can be disposable for one-time usage in conjunction with a TMJ or other procedure, or they can be adapted for sterilization and reuse.

A patient subsystem 5 includes an orthopedic or dental implant 8, which is adapted for placement in a patient 12 with an interspace 10 therebetween, which can receive suitable orthopedic cement for bonding the implant 8 in place.

Figure 1A:
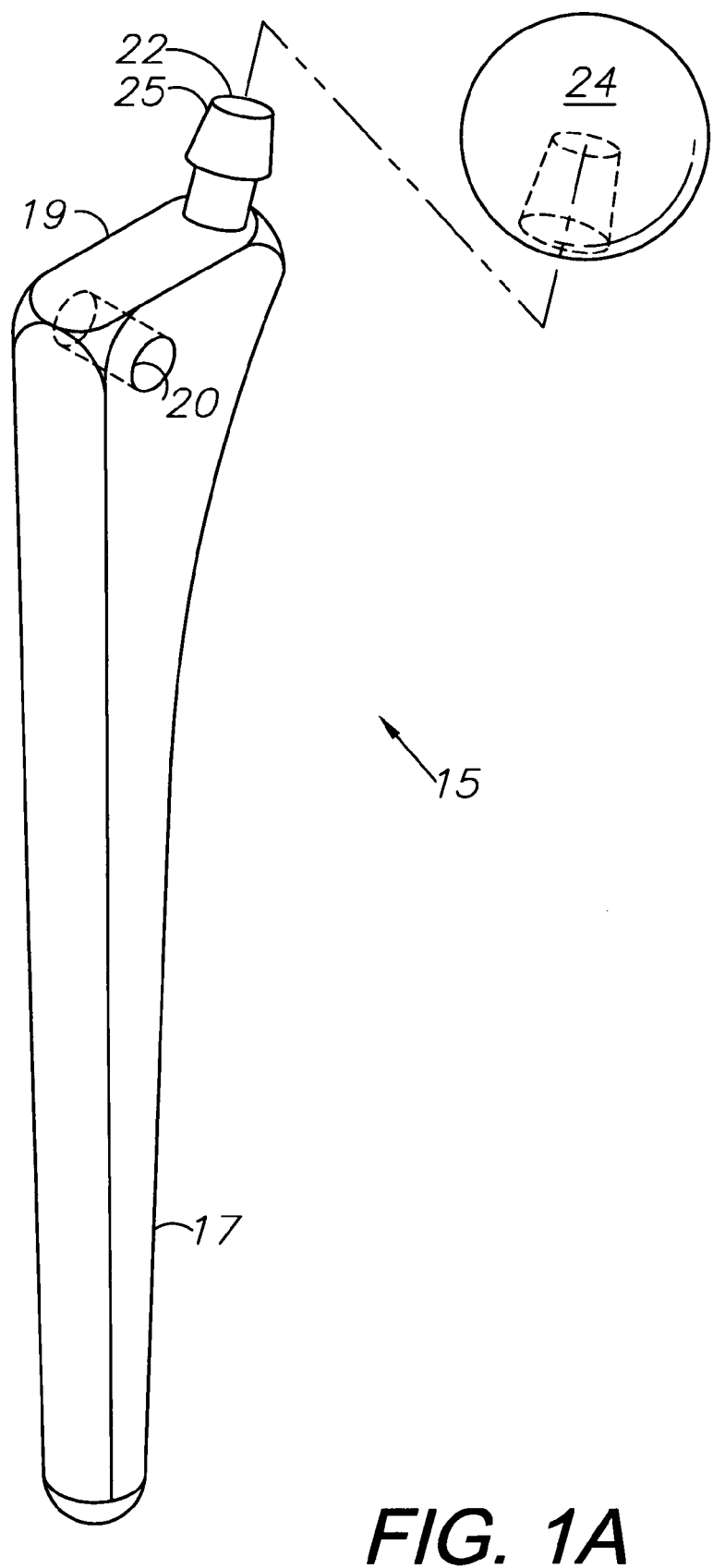
FIG. 1A is a perspective view of a hip femoral implant.

FIG. 1A shows a femoral implant 15, which can be used in a hip joint replacement procedure. The implant 15 includes an intramedullary canal shaft 17 integrally formed with a head 19 including a transverse passage 20. The shaft 17 can be finished with a scratch fit texture or engraving to facilitate bonding to bone. A stem 22 projects upwardly at an oblique angle from the head 19 and mounts a spherical cap 24 on a Morse taper 25. The cap 24 is pivotably received in an acetabular cup (not shown) to form a ball-and-socket type hip joint. Various configurations and designs of femoral and other implants can be used with the system of the present invention.

Transducer-To-Implant Couplings

Figure 2:
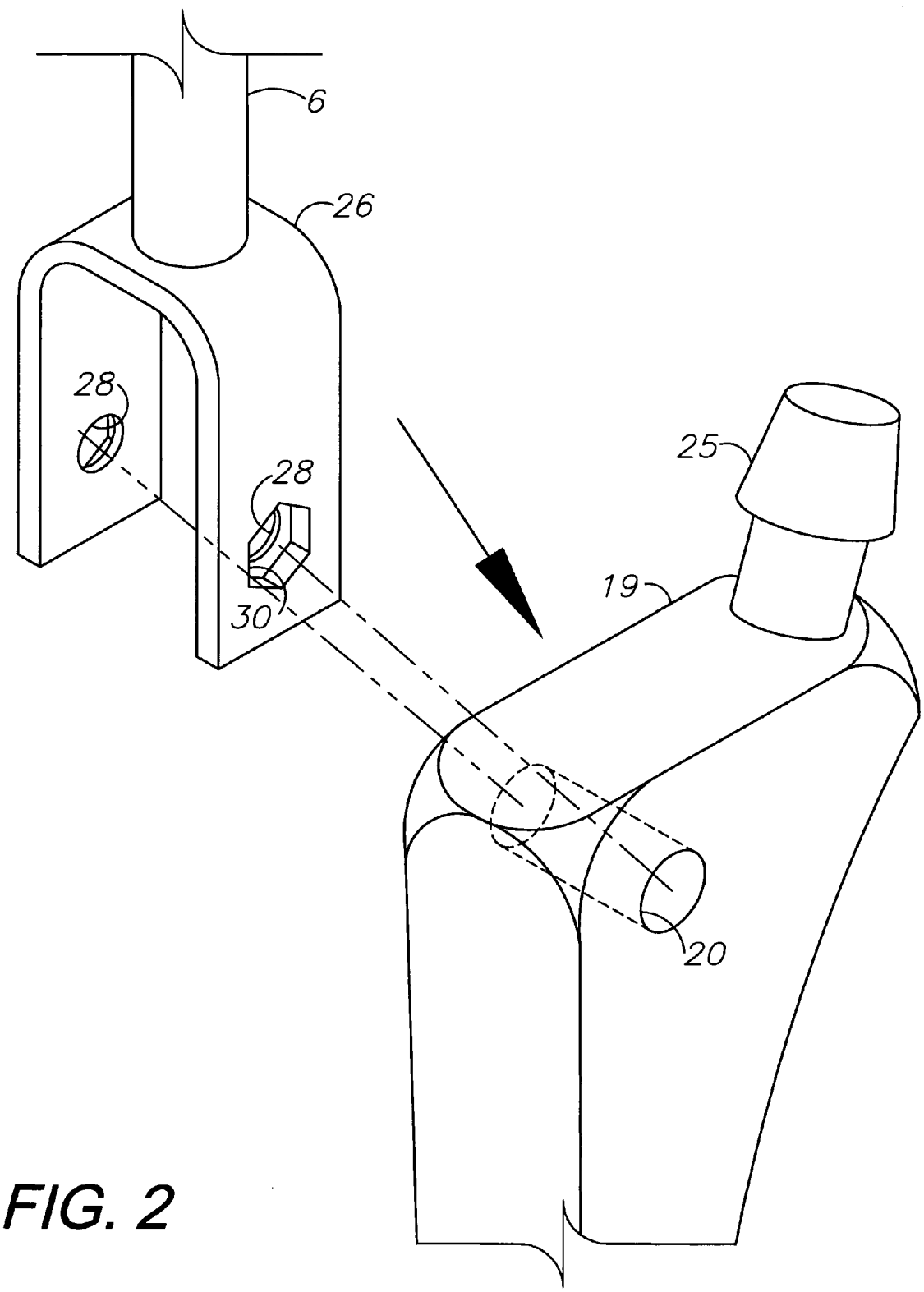
FIGS. 2-9 are fragmentary views of the coupling in the process of attachment to the implant.
Figure 3:
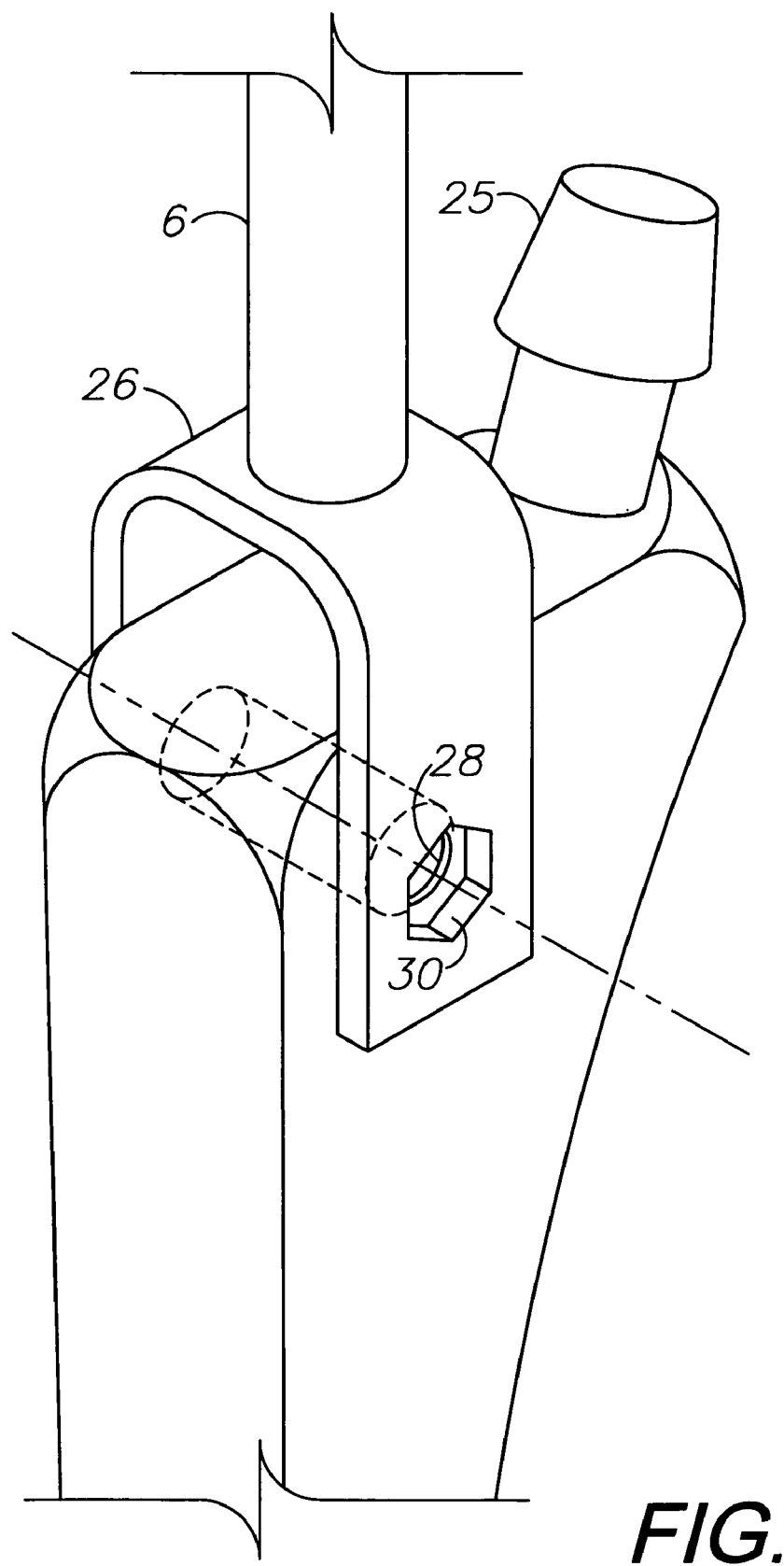
Figure 4:
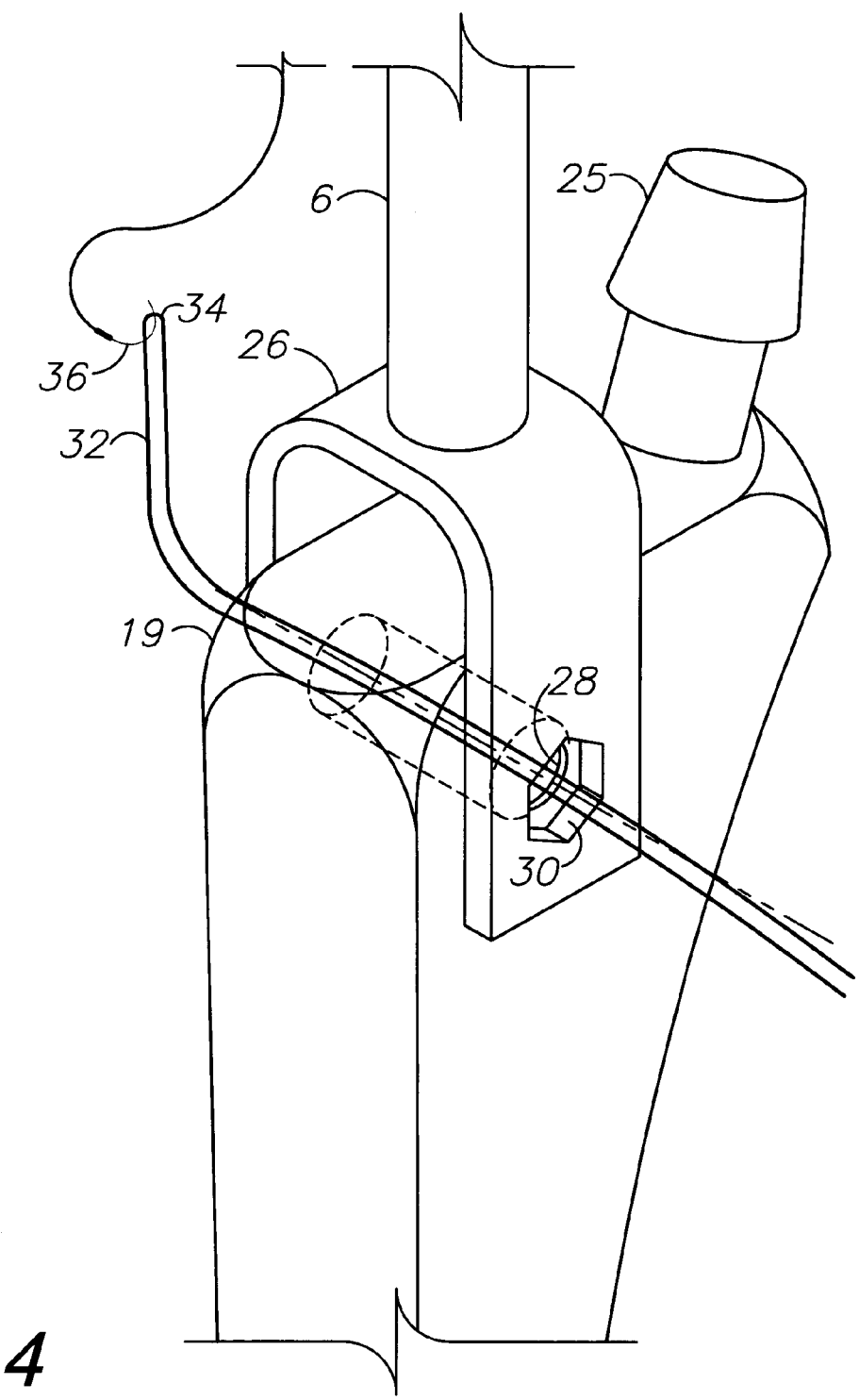
Figure 5:
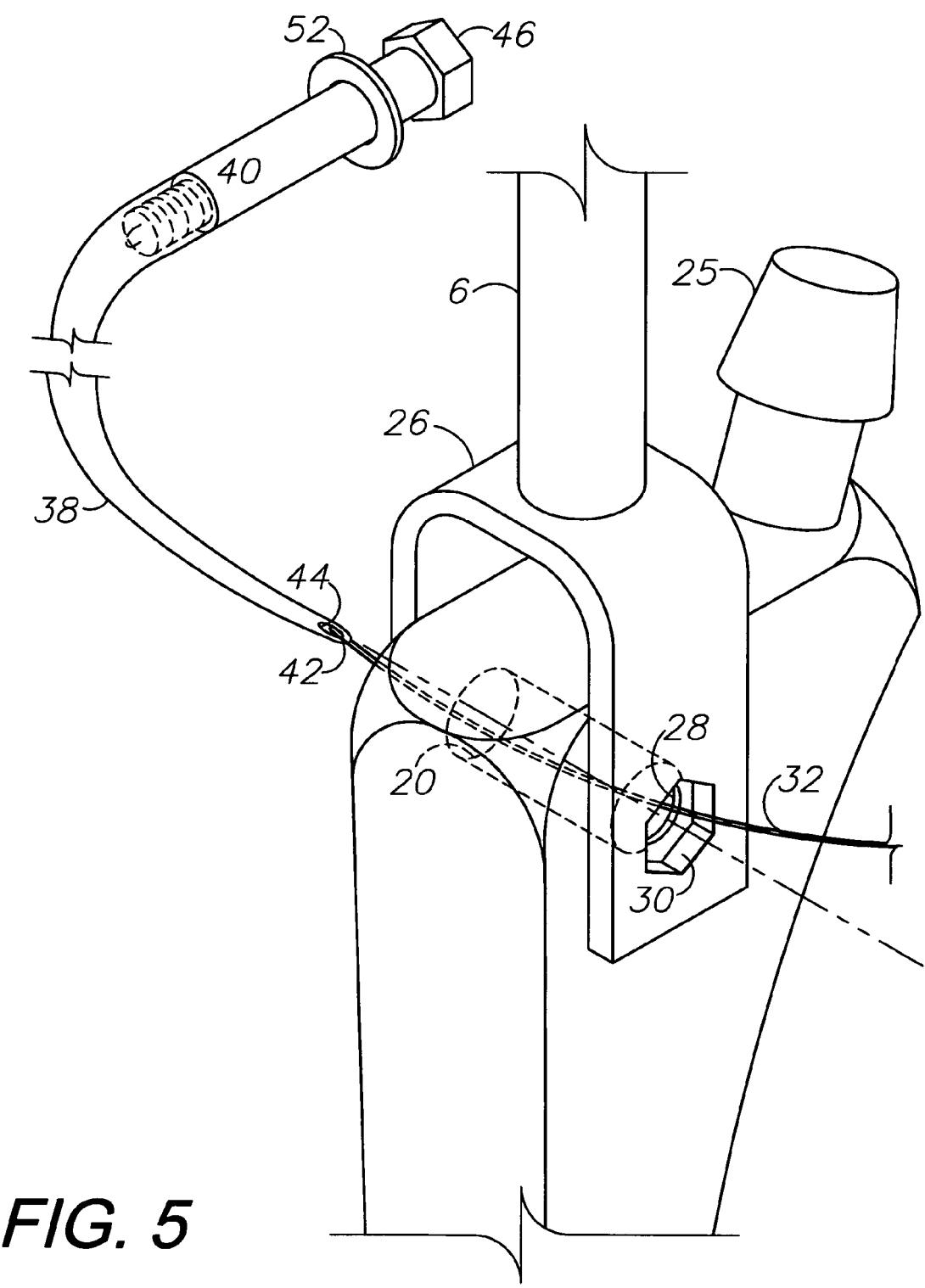
Figure 5A:
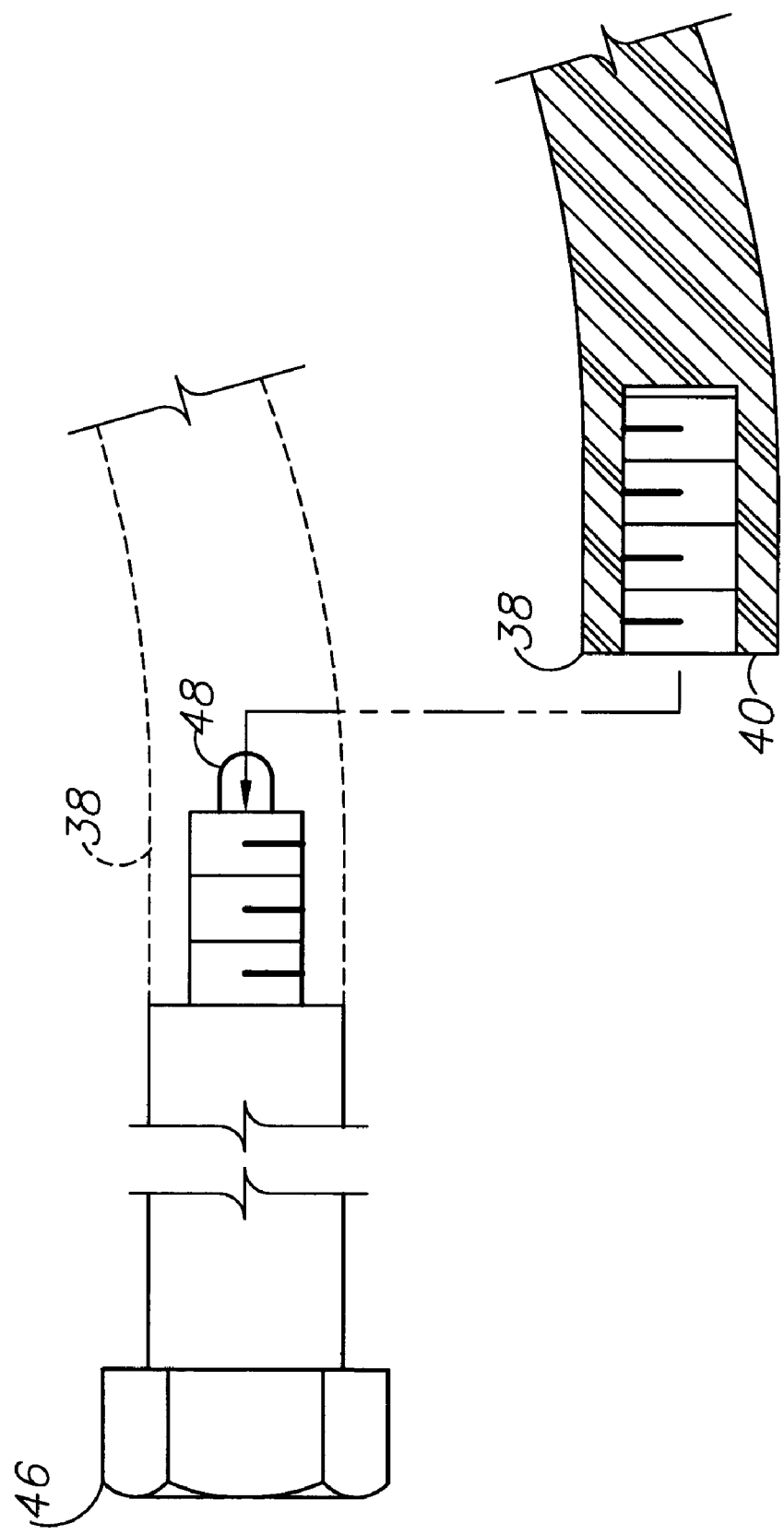

FIG. 2 shows a distal end 26 of the coupling 6 with a clevis configuration including a pair of receivers 28 with hexagonal recesses 30, which are adapted for alignment with the passage 20 (FIG. 3). FIG. 4 shows a guide wire 32 forming a loop 34 extending through the implant passage 20 and the coupling receivers 28. The loop 34 can be captured with a suture 36, which can be inserted into the patient from an entry location spaced from the entry location for the guide wire 32. FIGS. 5 and 5A show a flexible guide extension member 38, which tapers from a maximum diameter at a female-threaded base 40 to a minimum diameter at a pointed tip 42 with an eyelet 44. The guide member 38 is adapted for pulling a fastener, such as a bolt 46, through the aligned implant passage 20 and the clevis end receivers 28. The bolt 46 is threadably received in the guide member base 40 and the guide member eyelet 44 receives the guide wire 32, which is adapted for pulling the guide member 38 (FIG. 5). The flexibility of the guide member 38 enables it to approach the passage 20 and the receivers 28 from oblique angles.

Figure 6:
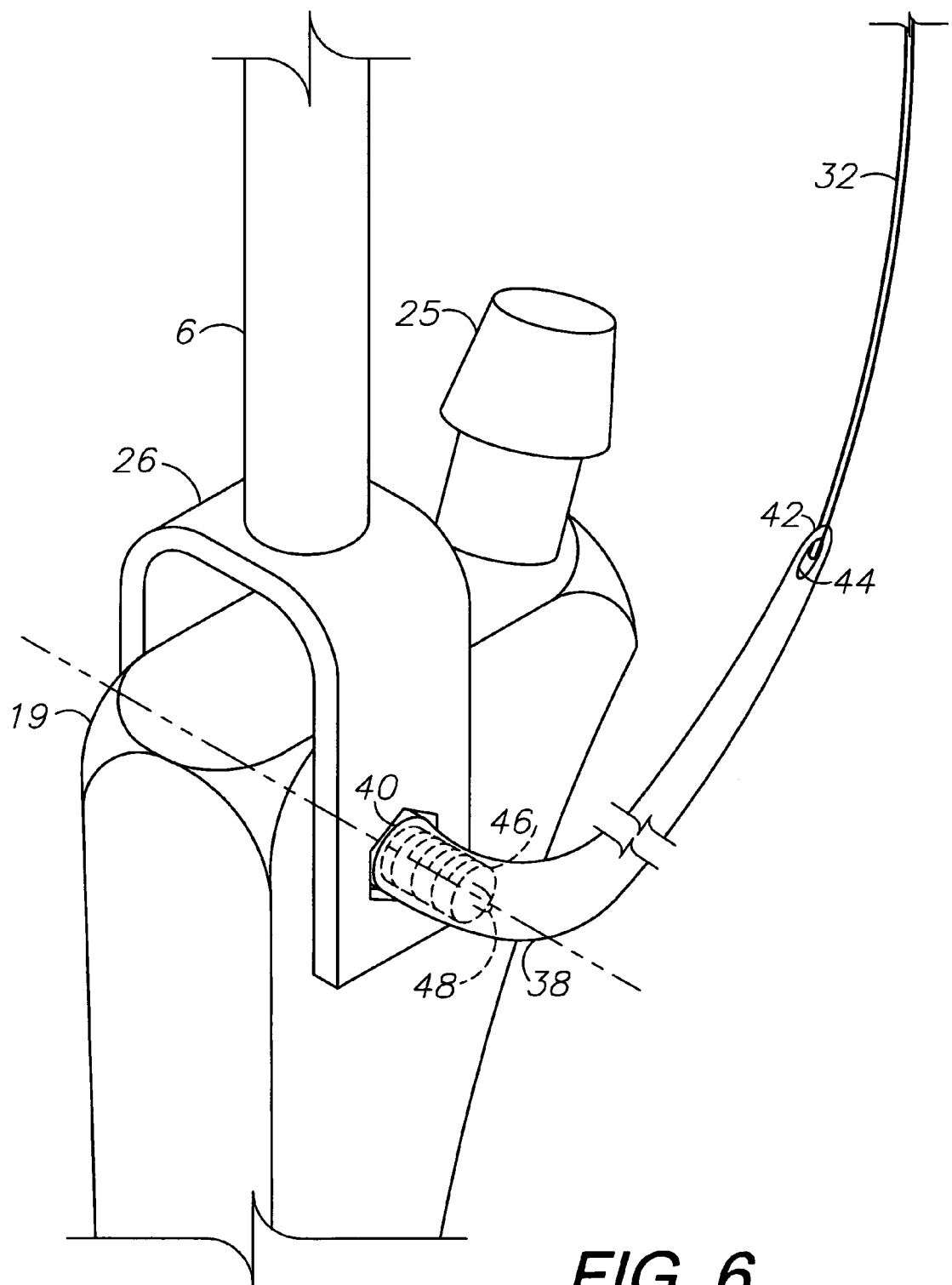
Figure 7:
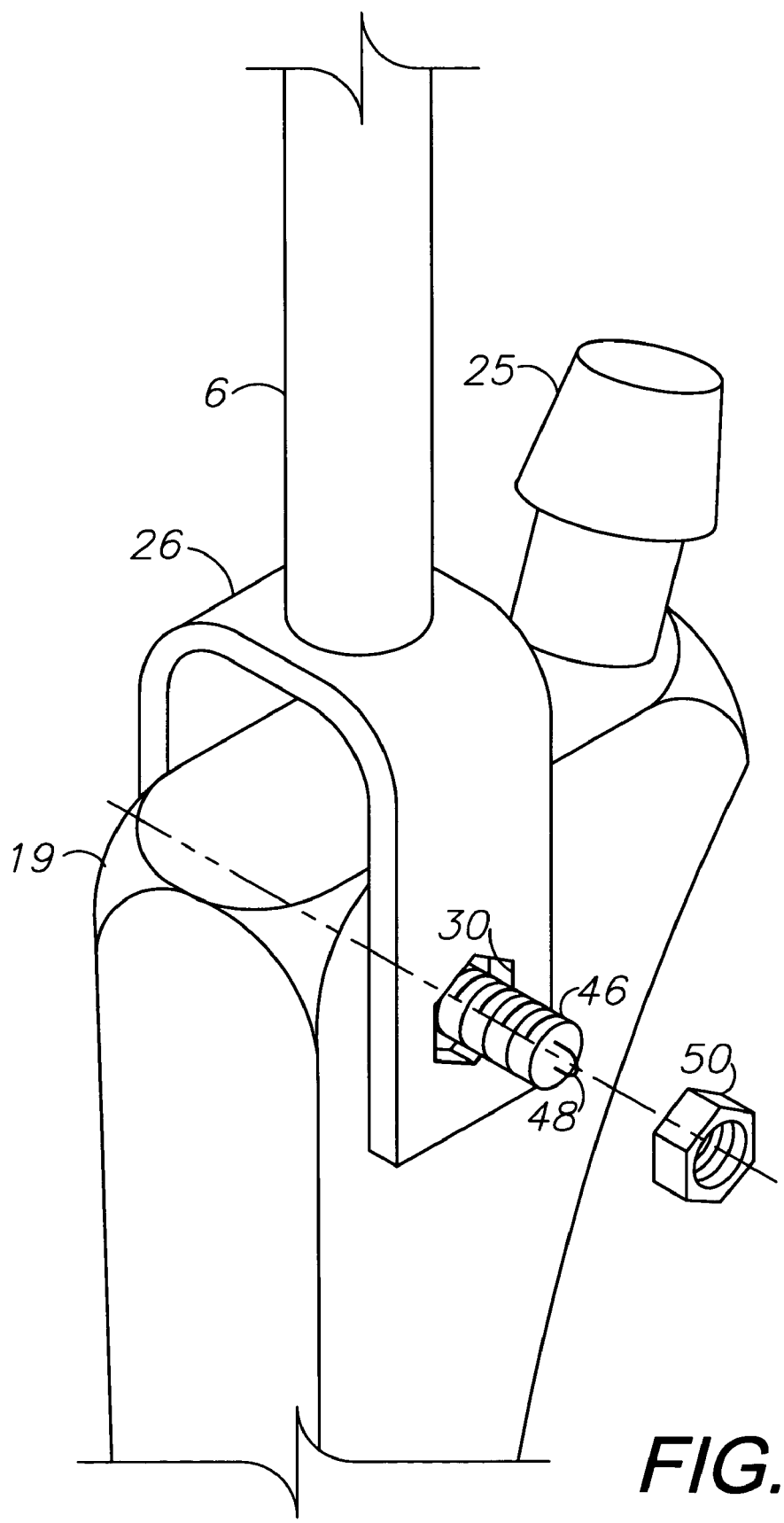
Figures 8, 9:
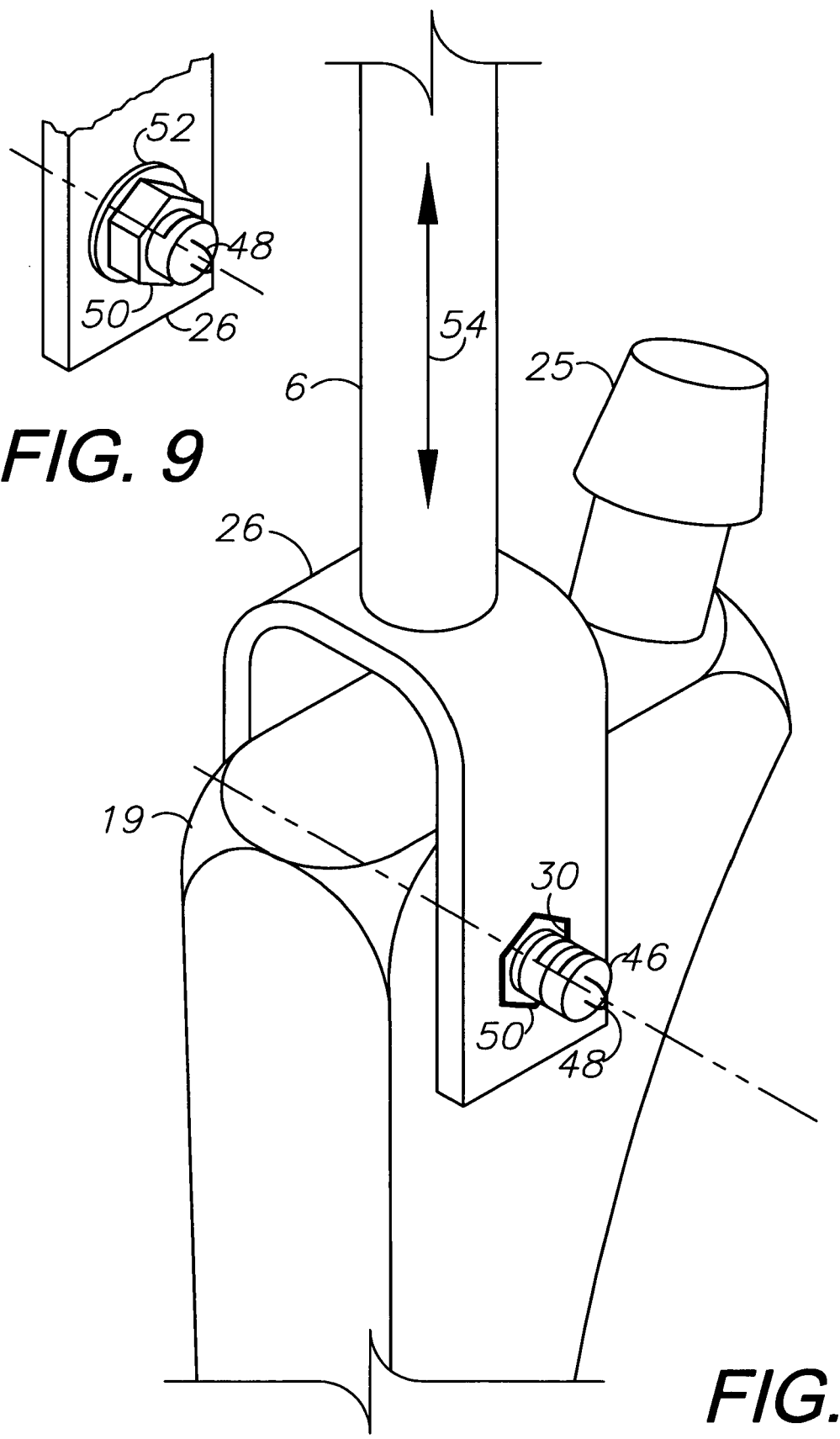
Figure 10:
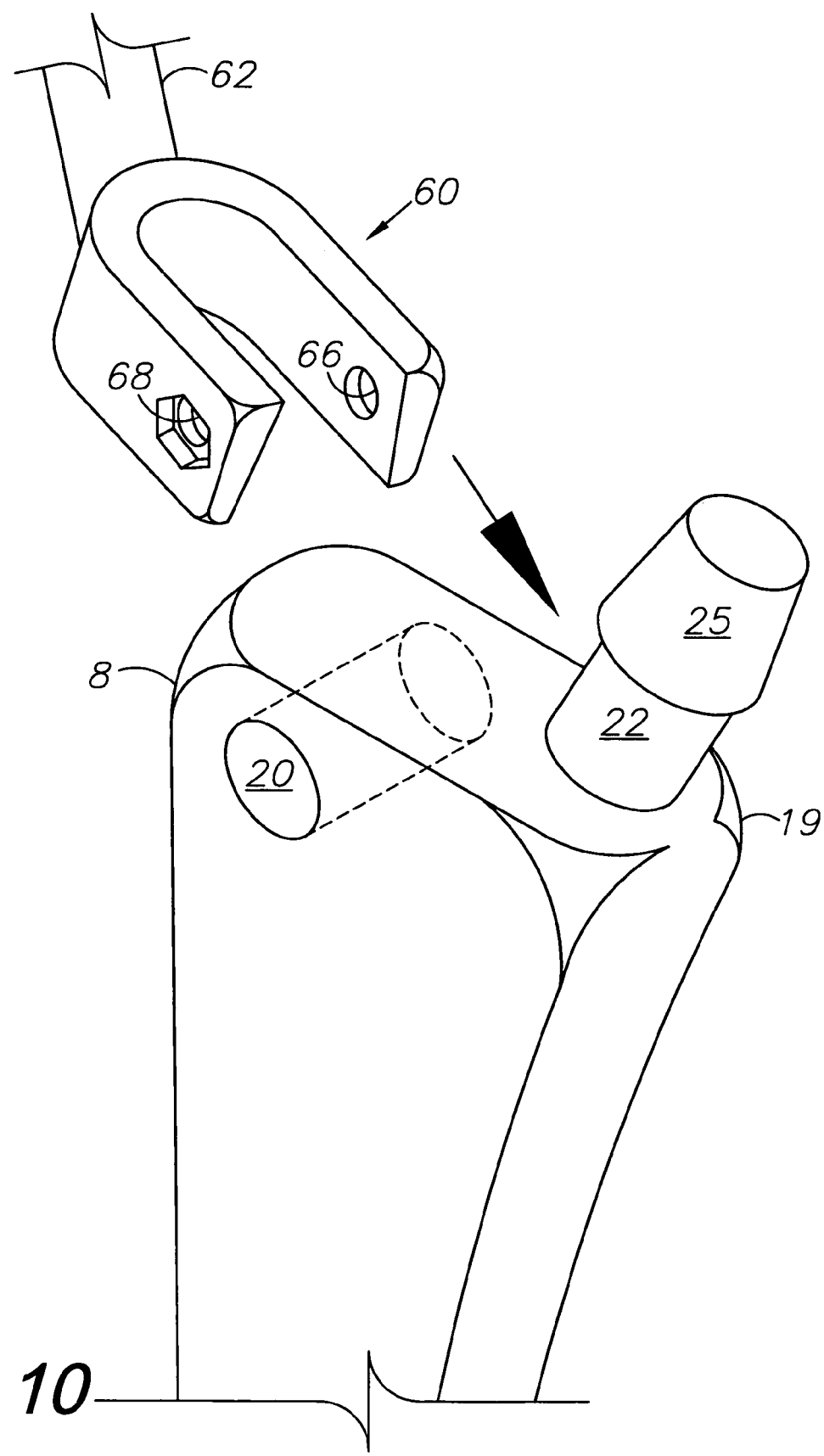
FIGS. 10-12 are fragmentary views of a coupling embodying another aspect of the invention, showing the process of attachment to the implant stem.
Figure 11:
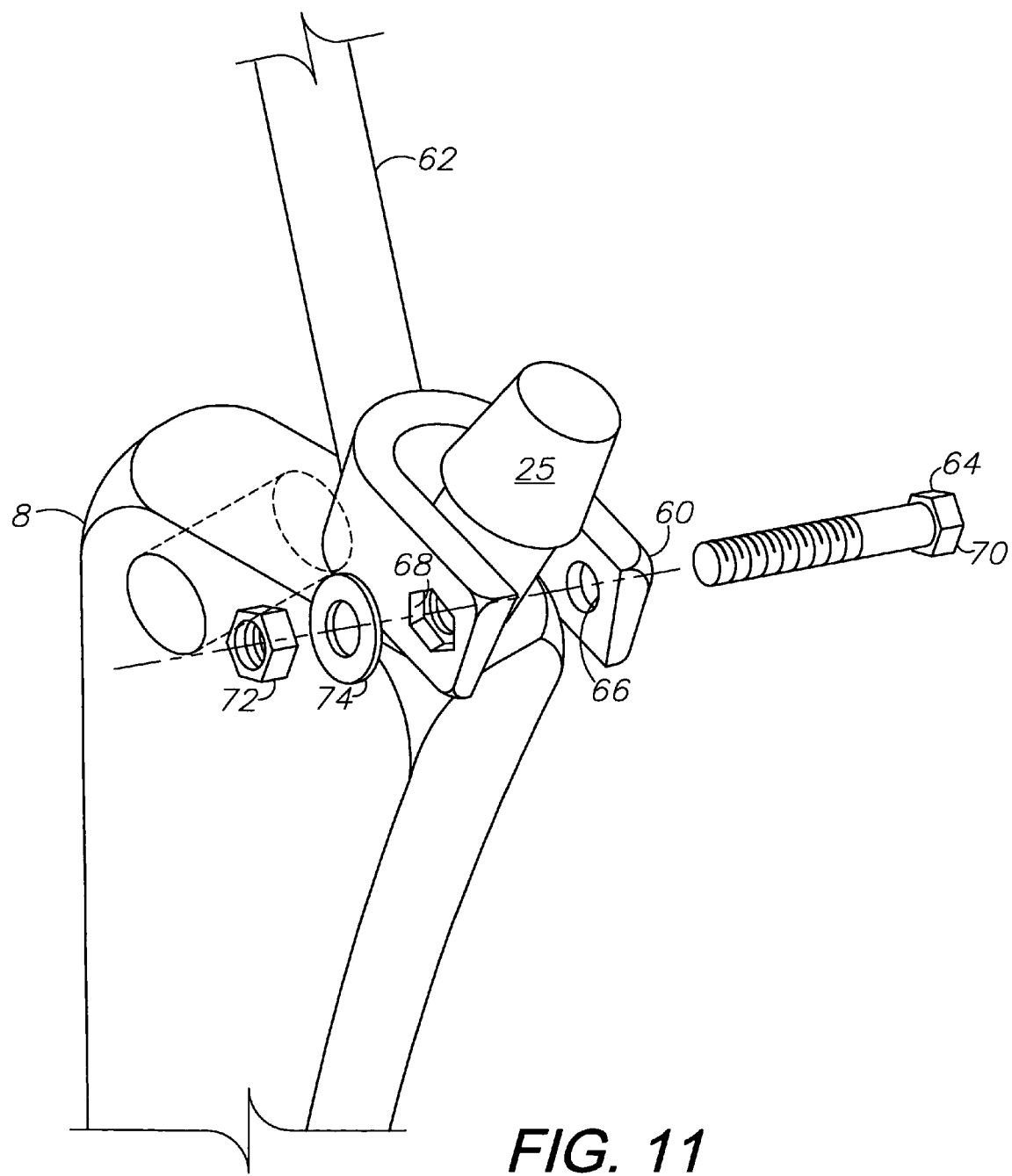
Figure 12:
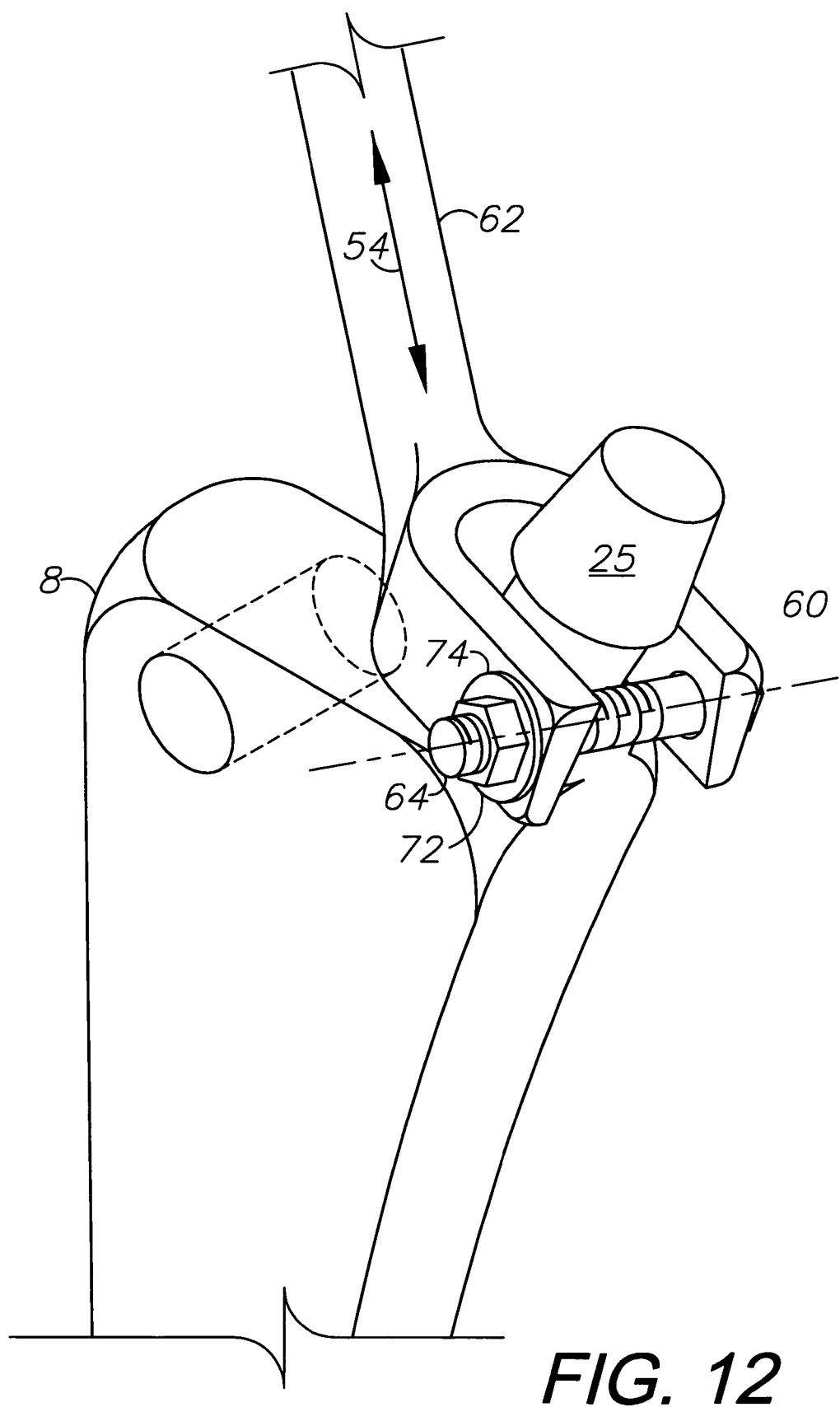

FIG. 6 shows the bolt 46 in place, with the guide member 38 extending therefrom. The bolt 46 includes a bolt loop 48 extending from its threaded end and adapted to capture the guide wire 32 or a suture to provide an alternative or auxiliary technique for installing the bolt 46. A nut 50 is threadably received on the end of the bolt 46 and can be drawn into the hexagonal recesses 30 (FIGS. 7 and 8), or surface-mounted on the clevis 26 (FIG. 9) with a washer 52.

The coupling distal, clevis end 26 transmits force from the force transducer 4 to the implant 8, as shown by the double-ended force arrow 54 (FIG. 8), which represents the application of linear, reciprocating "in" strokes 14, "out" strokes 16, or both (FIG. 1). As noted above, such forces can also be rotary reciprocating, oscillatory (side-to-side) or orbital. In operation such forces can be applied as necessary by the physician installing or extracting the implant 8. Moreover, test fitting same is facilitated with reduced risk of the implant becoming irretrievably stuck in an overly-tight intramedullary canal.

Figure 14:
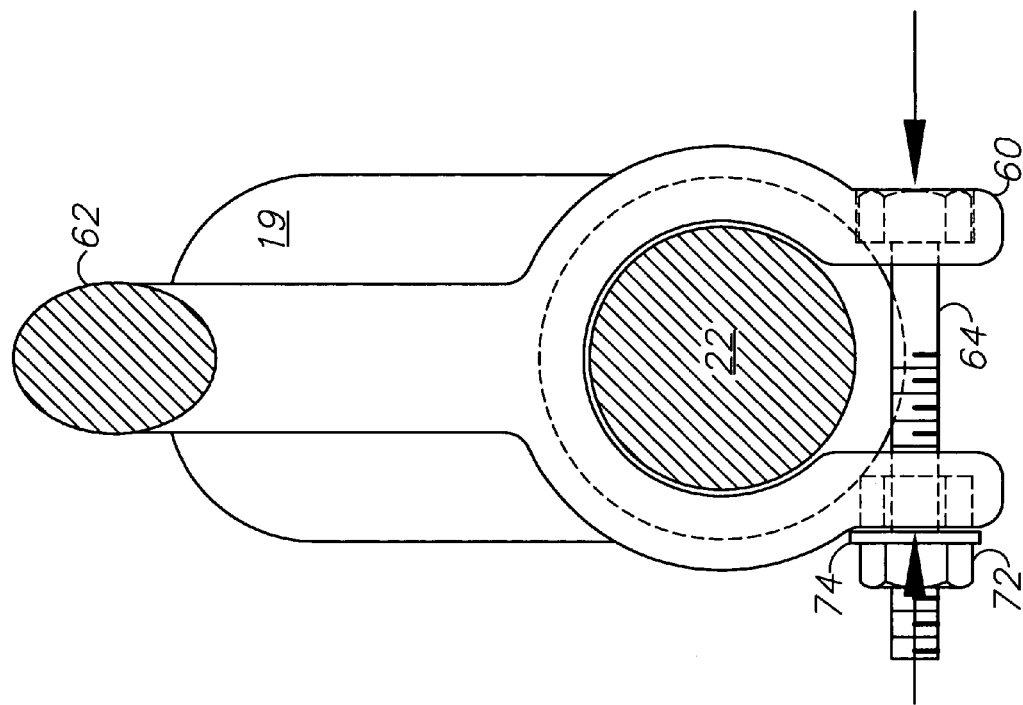
FIG. 14 is a top plan view of the coupling and the implant, with the coupling compressed onto the implant stem.
Figure 13:
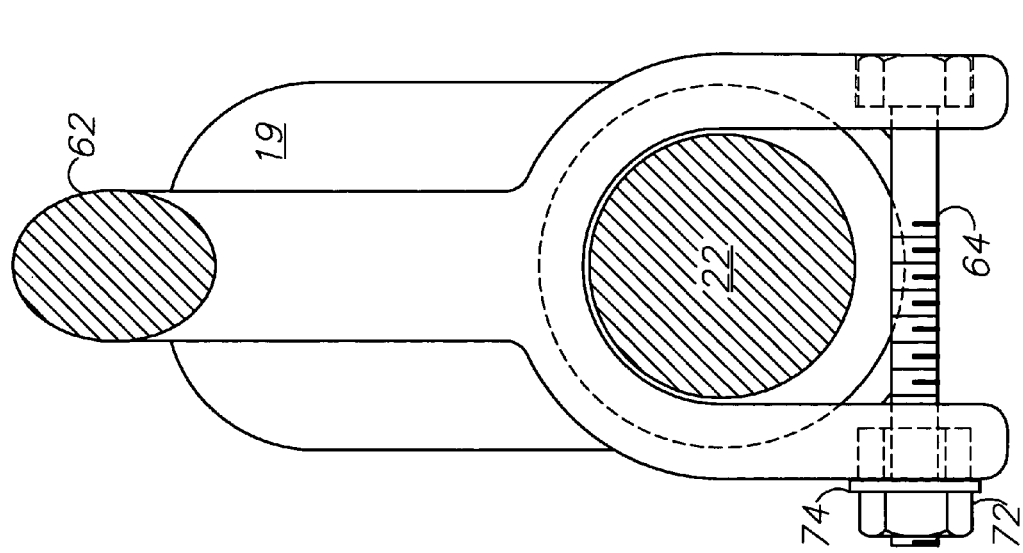
FIG. 13 is a top plan view of the coupling and the implant, taken generally along line 13-13 in FIG. 12.
Figure 15:
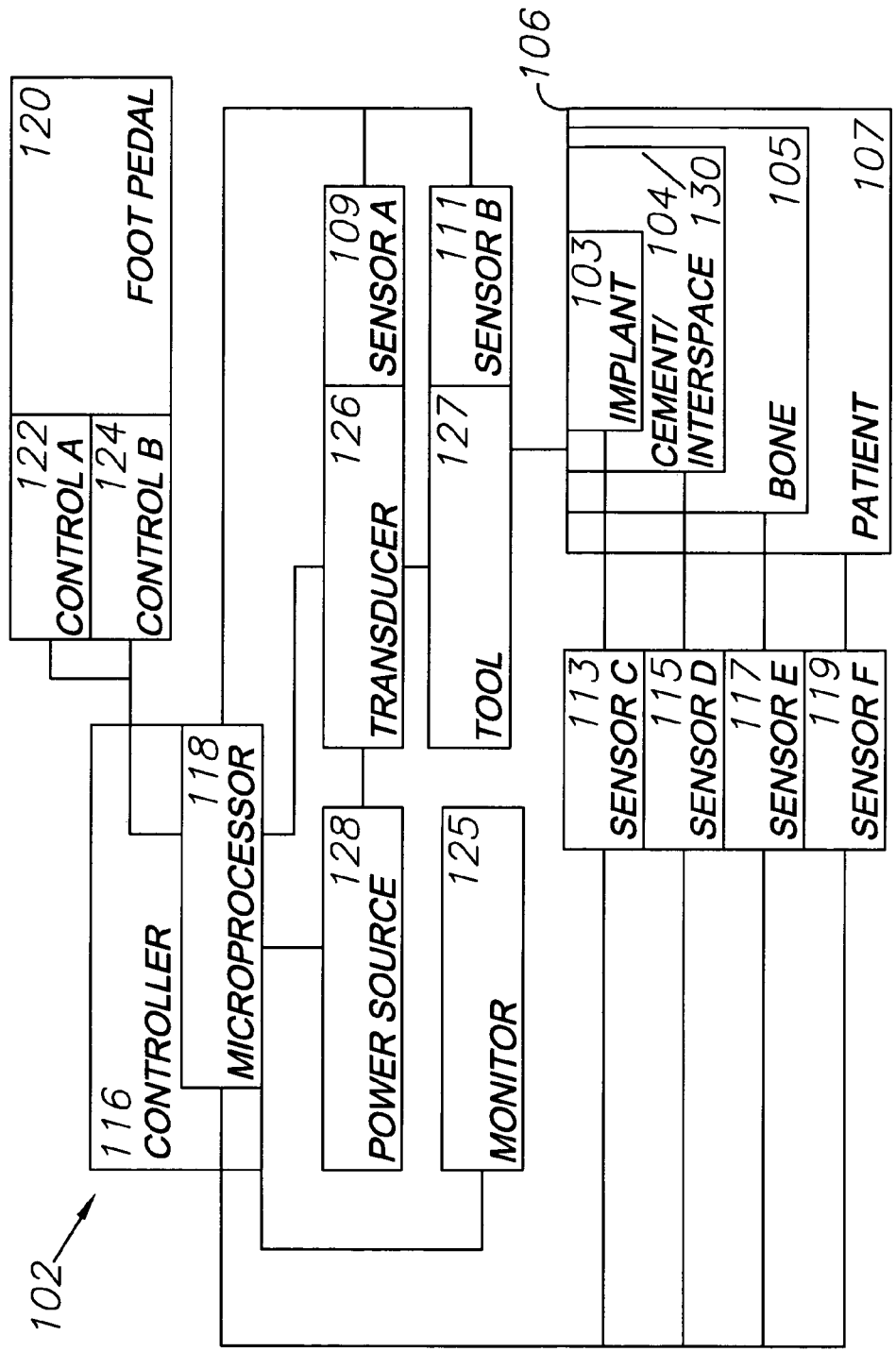
FIG. 15 is a block diagram of an automated system embodying another aspect of the present invention.

FIGS. 10-14 show an alternative configuration coupling distal end 60 comprising another aspect of the invention. The coupling end 60 has a clevis configuration with a shaft 62 extending at an oblique angle therefrom and connected to the force transducer 4. The coupling end 60 receives the implant stem 22 below a frusto-conical cap thereof and is clamped thereon (FIGS. 13-14) by a fastener, which can comprise a bolt received in coupling end receivers 66 and including hexagonal recesses for the bolt head 70 and a nut 72 (FIGS. 11 and 12), as required. A washer 74 can also be provided on either or both sides of the coupling end 60. As shown in FIG. 14, the coupling end 60 is deformable in order to securely clamp the implant stem 22.

Orthopedic Cement Extraction System and Method

A system 102 and a corresponding method comprising an alternative aspect of the present invention are shown in FIGS. 15-22 and are adapted for installing and removing orthopedic and dental implants 103 and orthopedic cement 104. Implants are commonly bonded in place with orthopedic cement, which may require removal in connection with revision procedures. For example, femoral implants are inserted into intramedullary canals and secured therein by cement.

Orthopedic cement 104 is placed in an interspace 130 around the implant 103 within the intramedullary canal of a bone 105 in a patient 107. Although an exemplary application of the invention is described in connection with a hip TJR, applications for same are virtually unlimited and include other replacement joints, such as knees, shoulders, etc.

The system 102 generally includes a controller 116 including a programmable microprocessor 118. The controller 116 can include various components, such as input and output devices, memory storage, etc. A foot pedal switch assembly 120 is connected to the controller 116 for providing input thereto and includes frequency and amplitude control switches 122, 124, which are adapted for hands-free operation by an operator pressing same with his or her feet, for example in a sterile operating environment.

A transducer 126 is controlled by the controller 116 and is operably connected to a tool 127 for imparting mechanical energy to the implant 103 and/or the cement 104. For example, the transducer 126 can provide rotorary reciprocating, linear reciprocating, oscillatory (side-to-side), orbital and other types of motion. The tool 127 can comprise a coupling, as described above, or various reciprocating and oscillatory saws, which are suitable for use with the system 102. Other types of tools include drills, vibrators and reciprocating chisels. The tool 127 is preferably designed for engaging the implant 103 or cutting, forming or shaping the cement 104, and can be used for dynamically coupling the transducer 126 to the implant 103 and/or the cement 104. A power source 128 provides power to the transducer 126 and can be controlled by the controller 116. The power source 128 can comprise electrical power, compressed air, compressed nitrogen, hydraulic fluid, etc.

The microprocessor 118 receives input signals from sensors 109, 111, 113, 115, 117 and 119 connected to the system components as shown in FIG. 1. For example, sensors 109, 111 provide feedback from the transducer 126 and the tool 127 respectively. The sensors 113, 115, 117 and 119 provide feedback from the implant 103, the cement 104, the bone 105 and the patient 107 respectively. It will be appreciated that fewer or more sensors can be utilized with the present invention, and can monitor and provide feedback with respect to the operation of various system components and the operating parameters associated with same. For example, the power load on the transducer 126 can be sensed for reaction by the controller 116, if necessary. Similarly, patient conditions such as temperature, blood pressure, stress indicators, etc. can be monitored and the microprocessor 118 can be preprogrammed to react to particular patient conditions and control the appropriate operating parameters of the system 102 whereby the primary functions thereof can be automated.

One or more of the sensors can comprise an energy-sensing device, such as an infrared thermal sensor. The controller 116 can be configured for thermally mapping the joint area whereby the temperature changes in the prosthetic joint 106, the patient 107 and the cement mantel 104 can be monitored in real-time. Such a thermal map can be displayed on a monitor 125 connected to the controller 116, which processes the thermal characteristics detected by the infrared thermal sensor as input for automatic control functions by the controller 116 and/or visual observation by means of the monitor 125.

Orthopedic Cement and Implant Extraction Method

Figure 16:
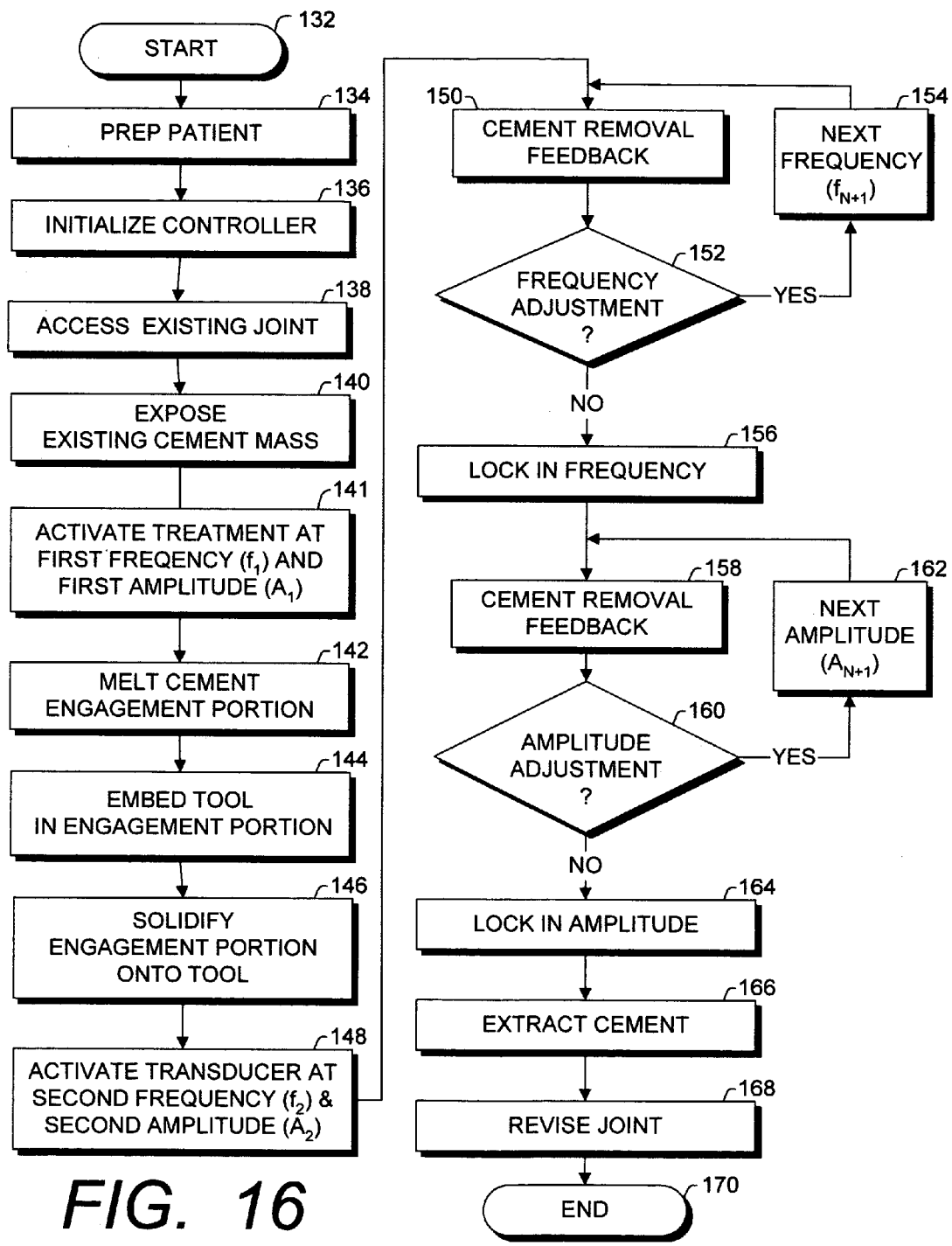
FIG. 16 is a flowchart showing an aspect of the method of the present invention.

FIG. 16 is a flowchart of a method embodying the present invention. From start 132 a patient 107 is prepared at 134 and the controller 116 is initialized at 136. Initializing the controller can include preprogramming certain operating parameters and conditions. For example, various common prostheses can be accommodated by preprogramming the controller to operate the transducer 126 at presumed optimum conditions, subject to varying the output signals to correspond to the actual conditions encountered. The existing joint 6 is accessed at 138 and the existing mass or mantel of cement 4 is exposed at 140. Polymethylmethacrylate (PMMA) cement is commonly used for implant attachment, particularly in medullary canals. Such cement is susceptible to softening when vibrated in the ultrasonic range, and tends to reform and reharden when the energy application is discontinued. The transducer 126 is activated at 141 and operates at a first frequency f1 and a first amplitude A1.

Accordingly, an engagement portion of the cement mantel 104 is melted at 142 and the tool 127 is embedded therein at 144. The melted engagement portion resolidifies at 146, thereby bonding the tool 127 to the cement mantel 104. The transducer 126 operates at a second frequency f2 and a second amplitude A2 at 148. For example, low-frequency vibration can be utilized to extract the cement. Feedback is received at 150. Such feedback can be derived from the various sensors 109, 111, 113, 115, 117, 119 and can correspond to such conditions as temperature and transducer current flow (corresponding to load conditions). For example, greater cement resistance to vibration can cause a greater load on the transducer 126, which in turn causes the current flow to increase. Such changing conditions can be sensed and predicted and can cause the controller 116 to respond accordingly. For example, upon encountering lessening resistance due to the cement mantel 104 softening, the controller 116 can reduce the amplitude of the energy applied to the transducer 126. Moreover, the resonant frequency of the components can be monitored. Frequency and amplitude changes can thus be detected and reacted to, for example by reducing or discontinuing the application of power.

It will be appreciated that the microprocessor 118 can be programmed to provide appropriate reactions to accommodate various operational parameters. For example, it is generally desirable to avoid excessive heat, which can damage both bone and soft tissue, thereby prolonging patient recovery. The microprocessor 118 can thus be programmed to reduce or cut off transducer power upon detecting certain conditions at any of several locations in the prosthetic joint or the patient. Moreover, manual inputs from the foot pedal switches 122, 124 or other operator-controlled inputs can be coordinated with automatic control features. For example, the operator can manually adjust such operating parameters as amplitude and frequency within predetermined operating ranges, beyond which automatic controls take over to avoid potential harm or discomfort to the patient.

If a frequency adjustment is indicated at decision box 152, the controller provides another frequency ($f_{n+1}$) at 154, and returns to the feedback step 150. When no further frequency adjustment is needed (negative branch from decision box 152), the method proceeds to lock in frequency at 156. Another feedback step occurs at 158 and leads to an amplitude adjustment decision box at 160, from which a positive decision leads to the next amplitude ($A_{n+1}$) being generated at 162. The negative branch from the decision box 160 leads to a lock in amplitude step at 164. Extraction occurs at 166, the joint is revised at 168 and the method terminates at 170.

Figure 18:
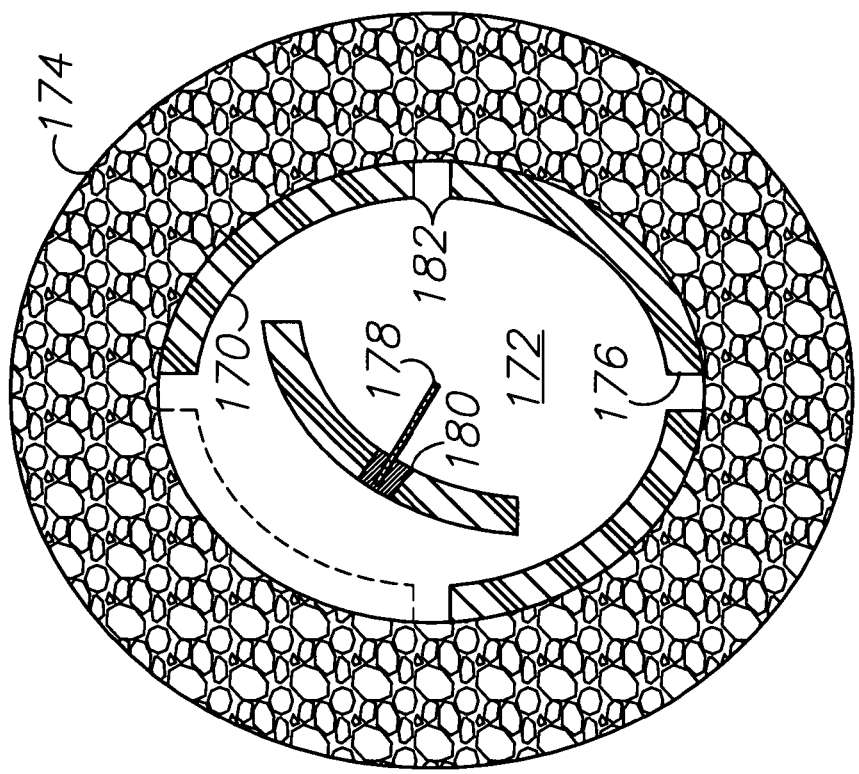
FIGS. 17-18 are cross-sectional views of a femur, showing an aspect of the method of the present invention for removing an orthopedic cement mantel from the intramedullary canal.
Figure 17:
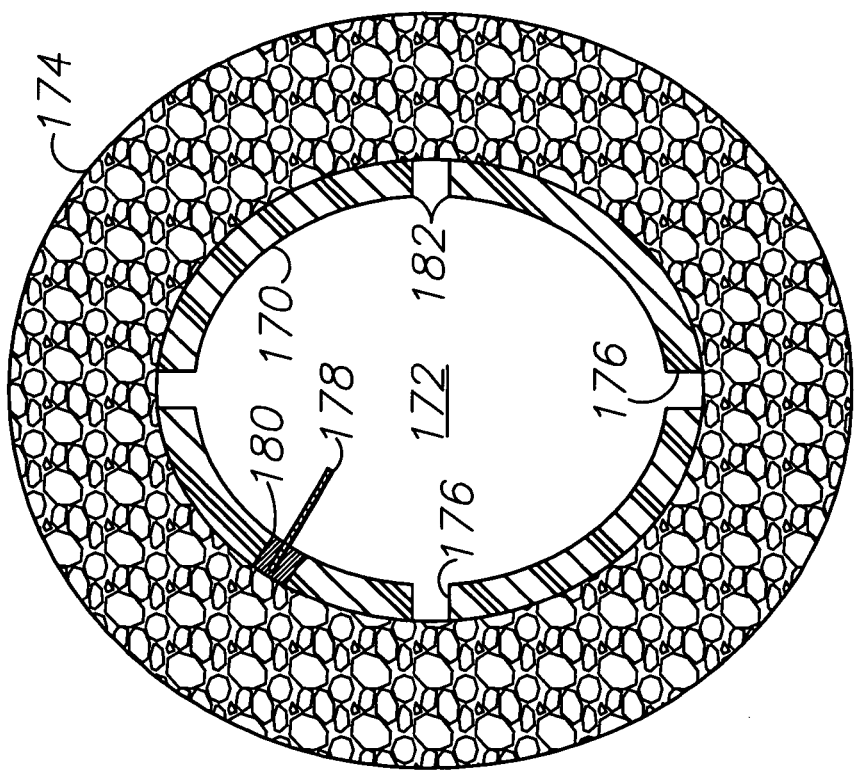

FIGS. 17-18 show applications of the cement removal system 102 and the method described above in connection with removing a cement mantel 170 from the intramedullary canal 172 in a femur 174. The mantel 170 is segmented with cuts 176. The blade 178 forms an engagement portion 180 whereat the liquefied cement 170 is permitted to solidify on the blade 178. The respective segments 182 can thus be extracted with the controlled application of force, such as low-frequency vibration, as shown in FIG. 18.

Figure 22:
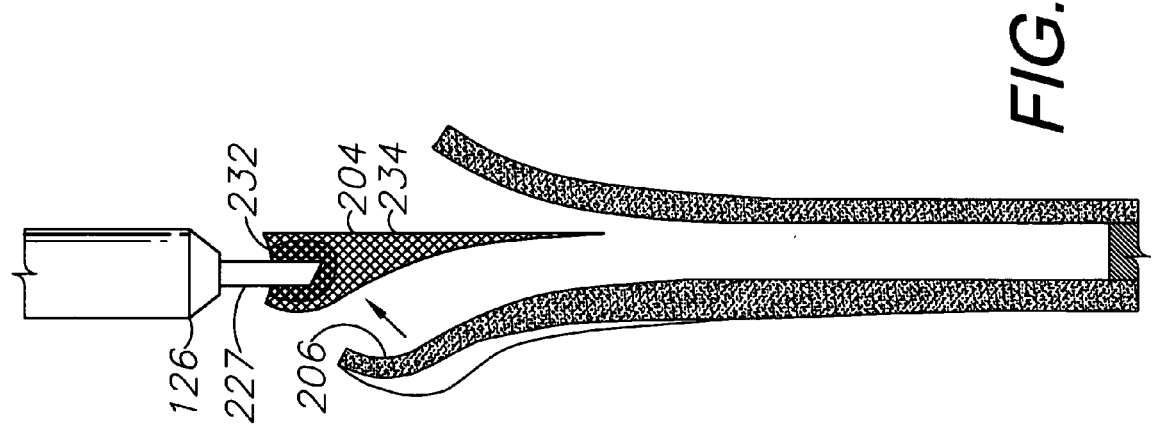
Figure 21:
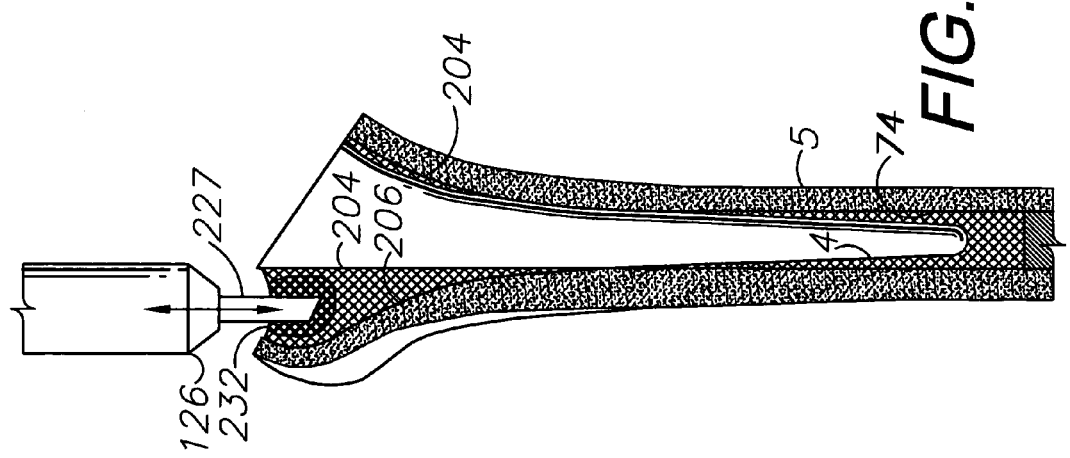

FIG. 19 shows a femur 210 and a femoral implant 208, which are separated by an interspace 230 filled with orthopedic cement 204. FIG. 20 shows the implant 208 removed, leaving the cement 204 within the intramedullary canal 206. As shown in FIG. 21, the tool 227 has penetrated an engagement portion 232 of the cement 204, which resolidifies to capture same. FIG. 22 shows a chunk 234 of cement 204 being removed from the intramedullary canal 206. By properly adjusting the frequency and amplitude of the transducer 126, substantial portions of the cement 204 can be removed. Upon completion of the extraction procedure, the walls of the intramedullary canal 206 are preferably free of cement 204, as shown in FIG. 22. The treating physician can then proceed with the revision procedure, including installation of replacement prosthetic components.

Although the system 102 and its methods of use have been described in connection with computer-controlled automation, the methods of the present invention can be practiced manually.

It is to be understood that while certain embodiments and/or aspects of the invention have been shown and described, the invention is not limited thereto and encompasses various other embodiments and aspects.

The invention claimed is:

1. A system for installing or extracting orthopedic or dental implants or cement from the bone structure of a patient, which system comprises:

a controller including an input adapted for receiving input signals and an output;

an input device adapted for providing an input signal to said controller;

a transducer connected to said controller output and adapted for providing a repeating, variable motion in response to an output signal from said controller;

a tool connected to said transducer and adapted for fixedly engaging said implant or said cement;

said controller automatically varying said output therefrom in response to inputs thereto from said input device, said controller inputs from said input device being automatically adjusted corresponding to operating conditions of said system associated with said implant or said cement; and said transducer and said tool being adapted for vibrating and installing or dislodging said implant or said cement from said patient bone structure.

2. The system according to claim 1, which includes:

said transducer having variable direction, frequency and amplitude, which are variably controlled by said controller.

3. The system according to claim 1, which includes:

a sensor adapted for connection to a patient and/or said transducer, said sensor being adapted to detect a condition associated with said patient and/or said transducer;

said sensor being connected to said controller input and providing said input signals thereat; and said controller being adapted to automatically vary the operating parameters of said transducer in response to controller input signals from said sensor.

4. The system according to claim 1 wherein said controller is adapted for automatically varying the frequency and amplitude of said transducer and is further adapted for adapted for locking in an optimum frequency and amplitude for installing or extracting said implant or said cement.

* * * * *